(12) United States Patent
Nathan

(10) Patent No.: US 6,872,799 B2
(45) Date of Patent: Mar. 29, 2005

(54) FUNCTIONALIZED POLYMERS FOR MEDICAL APPLICATIONS

(75) Inventor: Aruna Nathan, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/322,154

(22) Filed: Dec. 18, 2002

(65) Prior Publication Data

US 2004/0120927 A1 Jun. 24, 2004

(51) Int. Cl.$^7$ ............................................. C08G 63/02
(52) U.S. Cl. ........................ 528/272; 528/290; 528/306
(58) Field of Search ............................. 424/426, 85.7, 424/85.2, 85.4 BBB; 528/272, 288, 289, 290, 296, 299, 306

(56) References Cited

U.S. PATENT DOCUMENTS

| | | |
|---|---|---|
| 2,895,930 A | 7/1959 | Milton |
| 3,278,464 A | 10/1966 | Boyer et al. |
| 3,806,479 A | 4/1974 | Cunningham et al. |
| 3,978,203 A | 8/1976 | Wise |
| 3,997,512 A | 12/1976 | Casey et al. |
| 4,048,256 A | 9/1977 | Casey et al. |
| 4,076,798 A | 2/1978 | Casey et al. |
| 4,095,600 A | 6/1978 | Casey et al. |
| 4,118,470 A | 10/1978 | Casey et al. |
| 4,122,129 A | 10/1978 | Casey et al. |
| 4,163,073 A | 7/1979 | Pepe et al. |
| 4,384,975 A | 5/1983 | Fong |
| 4,419,139 A | 12/1983 | Gooch et al. |
| 4,568,559 A | 2/1986 | Nuwayser et al. |
| 5,137,743 A | 8/1992 | Zaks et al. |
| 5,155,246 A | 10/1992 | Naskar et al. |
| 5,219,980 A | 6/1993 | Swidler |
| 5,306,311 A | 4/1994 | Stone et al. |
| 5,308,623 A * | 5/1994 | Fues et al. .................. 424/426 |
| 5,360,626 A | 11/1994 | Iyengar et al. |
| 5,411,554 A | 5/1995 | Sopelianos et al. |
| 5,442,033 A | 8/1995 | Bezwada et al. |
| 5,464,929 A | 11/1995 | Bezwada et al. |
| 5,525,646 A | 6/1996 | Lundgren et al. |
| 5,599,852 A | 2/1997 | Sopelianos et al. |
| 5,607,687 A | 3/1997 | Bezwada et al. |
| 5,618,552 A | 4/1997 | Bezwada et al. |
| 5,628,993 A | 5/1997 | Yamagata et al. |
| 5,631,015 A | 5/1997 | Bezwada et al. |
| 5,653,992 A | 8/1997 | Bezwada et al. |
| 5,670,478 A | 9/1997 | Stuchlik et al. |
| 5,698,213 A | 12/1997 | Jamiolkowski et al. |
| 5,700,583 A | 12/1997 | Jamiolkowski et al. |
| 5,725,881 A | 3/1998 | Buchholz et al. |
| 5,728,752 A | 3/1998 | Scopelianos et al. |
| 5,750,100 A | 5/1998 | Yamagata et al. |
| 5,753,234 A | 5/1998 | Lee et al. |
| 5,824,333 A | 10/1998 | Scopelianos et al. |
| 5,859,150 A | 1/1999 | Jamiolkowski et al. |
| 5,998,552 A | 12/1999 | Gruber et al. |
| 6,074,660 A | 6/2000 | Jamiolkowski et al. |
| 6,100,346 A | 8/2000 | Jamiolkowski et al. |
| 6,110,501 A | 8/2000 | Redding, Jr. et al. |
| 6,114,458 A | 9/2000 | Hawker et al. |
| 6,120,787 A | 9/2000 | Gustafsson et al. |
| 6,121,398 A | 9/2000 | Wool et al. |
| 6,147,168 A | 11/2000 | Jamiolkowski et al. |
| 6,224,894 B1 | 5/2001 | Jamiolkowski et al. |
| 6,251,435 B1 | 6/2001 | Jamiolkowski et al. |
| 6,268,329 B1 | 7/2001 | Markussen |
| 6,335,383 B1 | 1/2002 | Scopelianos et al. |
| 2001/0007771 A1 | 7/2001 | Sullivan et al. |
| 2001/0021377 A1 | 9/2001 | Jamiolkowski et al. |
| 2002/0037301 A1 | 3/2002 | De La Poterie |
| 2003/0185752 A1 | 10/2003 | Nathan et al. |
| 2003/0185871 A1 * | 10/2003 | Nathan et al. ............... 424/426 |
| 2003/0236310 A1 * | 12/2003 | Nathan et al. ............ 514/772.4 |

FOREIGN PATENT DOCUMENTS

| | | |
|---|---|---|
| DE | 1694845 A | 8/1971 |
| EP | 0422209 B1 | 3/1995 |
| EP | 841361 A1 | 5/1995 |
| EP | 747072 A | 12/1996 |
| EP | 1270024 A | 1/2003 |
| EP | 1348451 A | 10/2003 |
| EP | 1369136 A | 12/2003 |
| EP | 1374860 A | 1/2004 |
| GB | 630924 A | 10/1949 |
| WO | WO 88/03785 A1 | 6/1988 |
| WO | WO 89/08894 A1 | 9/1989 |
| WO | WO 90/12604 A1 | 11/1990 |
| WO | WO 92/12645 A1 | 8/1992 |
| WO | WO 93/08850 A1 | 5/1993 |
| WO | WO 94/25079 A1 | 11/1994 |
| WO | WO 94/15079 A1 | 11/1995 |
| WO | WO 95/33821 A1 | 12/1995 |
| WO | WO 97/09367 | 3/1997 |
| WO | WO 97/23606 A1 | 7/1997 |
| WO | WO 99/29303 A1 | 6/1999 |
| WO | WO 00/02950 A1 | 1/2000 |
| WO | WO 00/35511 A | 6/2000 |
| WO | WO 00/44808 A1 | 8/2000 |
| WO | WO 01/07486 A1 | 2/2001 |
| WO | WO 01/76649 A | 10/2001 |

OTHER PUBLICATIONS

Database WPI Week 199430 Derwent Publications Ltd., London, GB; an 1994–248859 XP002256761 & WO 94 15591 A. (Hisamilsu), Jul. 12, 1994 abstract.

Mark H.F.: "Alkyd Resins", Encyclodpedia of Polmer Sience and Engineering. A to Amorphous Polymers, New York, J. Wiley & Sons, US. vol. 1, pp. 644–648 xP002035651 *the whole document*.

(Continued)

Primary Examiner—Tatyana Zalukaeva

(57) ABSTRACT

The present invention is directed to synthetic, biodegradable, biocompatible polymers that are the reaction product of an α,β-unsaturated polybasic acid or derivative thereof and a monoglyceride, and which further contain pended thereto a functional agent, and to medical devices and compositions containing such polymers.

10 Claims, No Drawings

OTHER PUBLICATIONS

Brian Parkyn F. Lamb and B. V. Clifton, "Polyesters vol. 2 Unsaturated Polyesters and Polyester Plasticisors," London Iliffe Books Ltd., New York American Elsevier ublishing Company, Inc., 1967 pp. 107–122.

Temple C. Patton, "Alkyd Resin Technology—Formulating Techniques and Allied Calculations," Interscience Publishers, a of John Wiley and Sons, New York—London 1962, pp. 13–31.

Emiko Koyama, Fumio Sanda, and Takeshi Endo, "Synthesis of Poly(ester–amide)s Derived from Optically Active Amino Alcohols," Macromol. Symp., 122, 275–280 (1997).

Emiko Koyama, Fumio Sanda, and Takeshi Endo, "Polycondensations of Hydroxycarboxylic Acids Derived from Optically Active Aminoalcohols and Acid Anhydrides—Syntheses of Functional Poly(ester–amide)s," Journal of Polymer–Science: Part A: Polymer Chemistry 35, 345–352 (1997).

Donald L. Elbert, Alison B. Pratt, Matthias P. Lutolf, Sven Halstenberg, Jeffrey A. Hubbell, "Protein Delivery from Materials Formed by Self–selective Conjugate Addition Reactions," Journal of Controlled Release, 76, 11–25 (2001).

U.S. Appl. No. 10/112,554, A. Nathan et al.

U.S. Appl. No. 10/162,933, A. Nathan.

U.S. Appl. No. 10/178,970, A. Nathan.

U.S. Appl. No. 10/183,260, J. Rosenbalt et al.

U.S. Appl. No. 10/322,132, A. Nathan.

U.S. Appl. No. 10/322,177, S.C. Arnold.

U.S. Appl. No. 10/325,768, A. Nathan.

U.S. Appl. No. 10/323,367, A. Nathan.

U.S. Appl. No. 10/112,201, A. Nathan et al.

* cited by examiner

FUNCTIONALIZED POLYMERS FOR MEDICAL APPLICATIONS

FIELD OF THE INVENTION

The present invention relates to synthetic, biodegradable, biocompatible polymers for use in pharmaceutical and medical applications and to compositions and medical devices containing such polymers.

BACKGROUND OF THE INVENTION

Both natural and synthetic polymers, including homopolymers and copolymers, which are both biocompatible and biodegradable in vivo are known for use in the manufacture of medical devices that are implanted in body tissue and that are absorbed or passed by the body over time. Examples of such medical devices include suture anchor devices, sutures, staples, surgical tacks, clips, plates, screws, drug-delivery devices, adhesion prevention films and foams, and tissue adhesives.

Natural polymers may include catgut, cellulose derivatives and collagen. Natural polymers typically are absorbed by the body after enzymatic degradation of the polymers in the body.

Synthetic polymers may include aliphatic polyesters, polyanhydrides and poly(orthoester)s. Such polymers typically degrade by a hydrolytic mechanism in the body and then are absorbed by the body. Such synthetic polymers include homopolymers, such as poly(glycolide), poly(lactide), poly(e-caprolactone), poly(trimethylene carbonate) and poly(p-dioxanone), and copolymers, such as poly(lactide-co-glycolide), poly(e-caprolactone-co-glycolide), poly(glycolide-co-trimethylene carbonate), poly(alkylene diglycolate), and polyoxaesters. The polymers may be statistically random copolymers, segmented copolymers, block copolymers or graft copolymers.

Alkyd-type polyesters prepared by the polycondensation of a polyol, polyacid and fatty acid are used in the coating industry in a variety of products, including chemical resins, enamels, varnishes and paints. These polyesters also are used in the food industry to make texturized oils and emulsions for use as fat substitutes.

While much progress has been made in the field of polymeric biomaterials, further developments must be made in order for such biomaterials to be used optimally in the body. There is a great need for polymers for use in drug delivery, tissue engineering and medical devices, where the polymers have functional pendant groups that would allow, e.g., attachment of drugs, improvement of biocompatibility or promotion of bioadhesion. Polyesters containing functional comonomers are known. However, the chemistry involved in the synthesis of functional monomers is often very complex and results in poor yields.

SUMMARY OF THE INVENTION

The present invention is directed to a synthetic, biodegradable, biocompatible polymer comprising the reaction product of an α,β-unsaturated polybasic acid or derivative thereof, a monoglyceride, and further comprising a functional agent pended thereto to provide the polymer with certain desired properties. The invention also is directed to compositions for medical applications and medical devices containing such polymers.

DETAILED DESCRIPTION OF THE INVENTION

Alkyd polymers have been prepared by several known methods. For example, alkyd-type polymers were prepared by Van Bemmelen (*J. Prakt. Chem.*, 69 (1856) 84) by condensing succinic anhydride with glycerol. In the "Fatty Acid" method (see Parkyn, et al. *Polyesters* (1967), Iliffe Books, London, Vol. 2 and Patton, In: *Alkyd Resins Technology*, Wiley-Interscience New York (1962)), a fatty acid, a polyol and an anhydride are mixed together and allowed to react. The "Fatty Acid-Monoglyceride" method includes a first step of esterifying the fatty acid with glycerol and, when the first reaction is complete, adding an acid anhydride. The reaction mixture then is heated and the polymerization reaction takes place. In the "Oil-Monoglyceride" method, an oil is reacted with glycerol to form a mixture of mono-, di-, and triglycerides. This mixture then is polymerized by reacting with an acid anhydride.

The synthetic, biodegradable, biocompatible polymers utilized in the present invention are the reaction product of an α,β-unsaturated polybasic acid or derivative thereof, a monoglyceride, and a functional agent. Preferably, the polymers of the present invention are prepared by the polycondensation first of an α,β-unsaturated polybasic acid or derivative thereof with a monoglyceride to form an alkyd polyester polymer. The monoglyceride comprises reactive hydroxy groups and fatty acid groups.

The alkyd polyester polymer is reacted with the functional agent to form the functionalized alkyd polyester of the present invention. The functional agent comprises a first functional moiety that is a strong nucleophile, such as a thiol or amine, that can react with the α,β-unsaturated acid through a Michael addition reaction, thus pending the functional agent to the polymer. A "strong nucleophile" is a molecule that is capable of donating an electron pair to an electrophile in a polar-bond forming reaction. Preferably, the strong nucleophile is more nucleophilic than $H_2O$ at physiologic pH.

The functional agent also comprises a second functional moiety, such as a hydroxyl, carboxyl, amine and the like, in order to provide the polymer with certain desired properties. For example; the functional agent may be selected to provide desired solubility properties or to adjust pH, depending upon the particular application. The functional agent may be selected based upon the ability of the second moiety's ability to react with certain therapeutic agents, e.g. pharmaceutical drugs. The second moiety also may provide desired hydrophobicity/hydrophilicity to the polymer. In addition, the adhesiveness of the polymer may be adjusted depending upon selection of the functional moiety.

The polymers comprise an aliphatic polyester backbone with pendant fatty acid ester groups on the monoglyceride unit and the second functional moiety, e.g. hydroxyl, carboxyl or amine, pendant from the diacid unit. Long chain saturated fatty acids result in polymers that are solids that exhibit relatively low melting points, e.g. between about 25° C. and 70° C. Alternatively, use of unsaturated fatty acids or short chain fatty acids results in liquid polymers. As used herein, a liquid polymer is a polymer with a melt temperature of less than about 25° C., preferably less than about 20° C.

The solid polymers and/or liquid polymers can be used to form injectable microdispersions. The microdispersions can be formed by physically blending either liquid polymers or finely ground solid polymers of the present invention with compatible polymers. In one embodiment, the microdispersions can be formed by physically blending liquid polymers of the present invention with finely ground solid polymers of the present invention. Upon blending, the solid polymer particle phase is dispersed through the polymeric liquid phase.

Generally, the solid polymers will have an average particle diameter of less than about 500 microns and preferably less than 50 microns. It is currently preferred to mix the finely ground solid polymer and the liquid polymer and raise the temperature of the mixture to a temperature sufficient to melt the solid polymer (melt blending), thereby providing a dispersion of a first polymeric liquid phase dispersed in a second polymeric liquid phase. Upon cooling, the first dispersed liquid polymeric phase participates to form a solid polymer phase dispersed in the second polymeric liquid phase. Melt blending is preferred because it simplifies the mixing operation involved in producing the microdispersion. It is desirable to avoid excessive heating during melt blending to avoid transesterification of the polymers.

Monoglycerides that may be used to prepare the polymers utilized in the present invention include, without limitation, monostearoyl glycerol, monopalmitoyl glycerol, monomyrisitoyl glycerol, monocaproyl glycerol, monodecanoyl glycerol, monolauroyl glycerol, monolinoleoyl glycerol, monooleoyl glycerol, and combinations thereof. Preferred monoglycerides include monostearoyl glycerol, monopalmitoyl glycerol and monomyrisitoyl glycerol.

$\alpha,\beta$-unsaturated polybasic acids that can be used include multifunctional carboxylic acids, such as maleic, fumaric, citraconic itaconic- acid and the like. Polybasic acid derivatives include anhydrides, such as maleic anhydride, mixed anhydrides, esters, activated esters and acid halides. The multifunctional carboxylic acids listed above are preferred.

In another embodiment, other polybasic acids such as succinic, glutaric, adipic, pimelic, suberic and sebacic acids could also be used to make copolymers with the $\alpha,\beta$-unsaturated acids listed above.

The functionalized alkyd polyesters of the present invention are made using the well known Michael addition reaction. The functional agent comprises a first functional moiety comprising a strong nucleophile, such as a thiol or amine, in order to provide reaction with and binding to the alkyd polyester. The functional agent also comprises a second functional moiety such as an alcohol, amine, acid, sulfate, solfonate and the like, in order to provide the functionalized alkyd polyester with certain properties. The choice of the functional agent will depend on the particular polymer to be generated and also upon the properties required for the particular anticipated or desired use of the functionalized polymer. One skilled in the art of medical devices and compositions, once having the benefit of this disclosure, will be able to readily ascertain the particular functional agent required for the particular properties desired under the particular circumstance. Suitable functional agents include, without limitation, mercaptoethanol, mercaptopropanol, mercaptobutanol, mercaptohexanol, mercaptopropanediol, mercaptoacetic acid, mercaptopropionic acid, mercaptosuccinic acid and mercaptoethylamine.

In certain embodiments of the invention, the alkyd polyester may be prepared from the polybasic acid or derivative thereof, the monoglyceride and, additionally, at least one additional polyol selected from the group consisting of ethylene glycol, 1,2-propylene glycol, 1,3-propanediol, bis-2-hydroxyethyl ether, 1,4-butanediol, 1,5-pentanediol, 1,6-hexanediol, 1,8-octanediol, 1,10-decanediol, 1,12-dodecanediol, other diols, linear poly(ethylene glycol), branched poly(ethylene glycol), linear poly(propylene glycol), branched poly(propylene glycol), linear poly(ethylene-co-propylene glycol)s and branched poly(ethylene-co-propylene glycol)s. In preparing the polymers of the present invention, the particular chemical and mechanical properties required of the polymer for a particular use must be considered. For example, changing the chemical composition can vary the physical and mechanical properties, including absorption times. Copolymers can be prepared by using mixtures of diacids, different monoalkanoyl glycerides and different functional moieties to match a desired set of properties. Similarly, blends of two or more functionalized alkyds may be prepared to tailor properties for different applications.

A variety of biological active substances, hereinafter referred to as bioactive agents, can be covalently attached to the functionalized polymers by known coupling chemistry to provide sustained release of the bioactive agent. As used herein, bioactive agent is meant to include those substances or materials that have a therapeutic effect on mammals, e.g. pharmaceutical compounds.

The polymerization of the alkyd polyesters preferably is performed under melt polycondensation conditions in the presence of an organometallic catalyst at elevated temperatures. The organometallic catalyst preferably is a tin-based catalyst, e.g. stannous octoate. The catalyst preferably will be present in the mixture at a mole ratio of polyol and polycarboxylic acid to catalyst in the range of from about 15,000/1 to 80,000/1. The reaction preferably is performed at a temperature no less than about 120° C. Higher polymerization temperatures may lead to further increases in the molecular weight of the copolymer, which may be desirable for numerous applications. The exact reaction conditions chosen will depend on numerous factors, including the properties of the polymer desired, the viscosity of the reaction mixture, and melting temperature of the polymer. The preferred reaction conditions of temperature, time and pressure can be readily determined by assessing these and other factors.

Generally, the reaction mixture will be maintained at about 180° C. The polymerization reaction can be allowed to proceed at this temperature until the desired molecular weight and percent conversion is achieved for the copolymer, which typically will take from about 15 minutes to 24 hours. Increasing the reaction temperature generally decreases the reaction time needed to achieve a particular molecular weight.

In another embodiment, copolymers of alkyd polyesters can be prepared by forming an alkyd polyester prepolymer polymerized under melt polycondensation conditions, then adding at least one lactone monomer or lactone prepolymer. The mixture then would be subjected to the desired conditions of temperature and time to copolymerize the prepolymer with the lactone monomers.

The molecular weight of the prepolymer, as well as its composition, can be varied depending on the desired characteristic that the prepolymer is to impart to the copolymer. Those skilled in the art will recognize that the alkyd polyester prepolymers described herein can also be made from mixtures of more than one monoglyceride and dicarboxylic acid.

The addition of the functional agent comprising the nucleophilic reagent to the alkyd polyester having an $\alpha,\beta$-unsaturated group can be carried out at room temperature or at 60° C. for 24 hours using benzoyl peroxide/dimethylaminopyridine or azobis isobutyronitrile (AIBN) as catalyst. Alternatively, the reaction may be performed at room temperature for 14 hours using triethylamine as catalyst.

The polymers, copolymers and blends of the present invention can be crosslinked to affect mechanical properties.

Crosslinking can be accomplished by the addition of crosslinking enhancers, irradiation, e.g. gamma-irradiation, or a combination of both. In particular, crosslinking can be used to control the amount of swelling that the materials of this invention experience in water.

One of the beneficial properties of the functionalized alkyd polyesters of this invention is that the ester linkages in the alkyd block are hydrolytically unstable and, therefore, the polymer is biodegradable because it readily breaks down into small segments when exposed to moist body tissue. The segments then either are absorbed by the body, or passed by the body. More particularly, the biodegraded segments do not elicit permanent chronic foreign body reaction, because they are absorbed by the body, such that no permanent trace or residual of the segment is retained by the body. In this regard, while it is envisioned that co-reactants could be incorporated into the reaction mixture of the polybasic acid and the diol for the formation of the functionalized alkyds, it is preferable that the reaction mixture does not contain a concentration of any co-reactant that would render the subsequently prepared polymer nonbiodegradable or non-absorbable. Preferably, the reaction mixture is substantially free of any such co-reactants if the resulting polymer is rendered nonbiodegradable or nonabsorbable.

The functionalized polymers of the present invention may be used in various medical devices for various purposes. One skilled in the art, once having the benefit of this disclosure, will be able to readily utilize the polymers in various medical devices. Examples of such medical devices include suture anchor devices, sutures, staples, surgical tacks, clips, plates, screws, drug-delivery devices, adhesion prevention films and foams, and tissue adhesives.

In one embodiment of the invention, the functionalized alkyd polyesters of the present invention can be used as a pharmaceutical carrier in a drug delivery matrix. Solid functionalized alkyd polyesters could be used to coat or encapsulate a bioactive agent. Alternatively, an effective amount of a bioactive agent could be mixed with injectable microdispersions of solid and liquid polymers. Such a microdispersion would be particularly suitable for unstable drugs such as proteins.

The variety of bioactive agents that can be used in conjunction with the polymers of the invention is vast. In general, bioactive agents which may be administered via pharmaceutical compositions of the invention include, without limitation, antiinfectives, such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, growth factors, polysaccharides, glycoproteins or lipoproteins; oligonucleotides; antibodies; antigens; cholinergics; chemotherapeutics; hemostatics; clot dissolving agents; radioactive agents; and cystostatics.

Rapamycin, risperidone, and erythropoietin are preferred bioactive agents that may be used in drug delivery matrices of the present invention.

The drug delivery matrix may be administered in any suitable dosage form such as oral, parenteral, pulmonary, buccal, nasal, ocular, topical, vaginal routes, or as a suppository. Bioerodible particles, ointments, gels, creams, and similar soft dosage forms adapted for the administration via the above routes may also be formulated. Other modes of administration, e.g. transdermal, and compositional forms, e.g. more rigid transdermal forms, are within the scope of the invention as well.

Parenteral administration of a bioerodible composition of the invention can be effected by either subcutaneous or intramuscular injection. The bioactive agent could be encapsulated in particles made of the solid polymer. Alternatively, parenteral formulations of the copolymer may be formulated by mixing one or more pharmaceuticals with a liquid copolymer or microdispersion. Other suitable parenteral additives may be formulated with the copolymer and pharmaceutical active. However, if water is to be used it should be added immediately before administration. Bioerodible ointment, gel or cream may also be injected as is or in combination with one or more suitable auxiliary components as described below. Parenteral delivery is preferred for administration of proteinaceous drugs such as growth factors, growth hormone, or the like.

The bioerodible ointments, gels and creams of the invention will include an ointment, gel or cream base comprising one or more of the copolymers described herein and a selected bioactive agent. The bioactive agent, whether present as a liquid, a finely divided solid, or any other physical form, is dispersed in the ointment, gel or cream base. Typically, but optionally, the compositions include one or more other components, e.g., nontoxic auxiliary substances such as colorants, diluents, odorants, carriers, excipients, stabilizers or the like.

The quantity and type of copolymers incorporated into the parenteral, ointment, gel, cream, etc., is variable. For a more viscous composition, a higher molecular weight polymer is used. If a less viscous composition is desired, a lower molecular weight polymer can be employed. The product may contain blends of the liquid or low melting point copolymers to provide the desired release profile or consistency to a given formulation.

While not essential for topical or transdermal administration of many drugs, in some cases, it may be preferred that a skin permeation enhancer be co-administered with the drug. Any number of the many skin permeation enhancers known in the art may be used. Examples of suitable enhancers include dimethylsulfoxide (DMSO), dimethylformamide (DMF), N,N-dimethylacetamide (DMA), deslymethylsulfoxide, ethanol, eucalyptol, lecithin, and the 1-N-dodecylcyclazacycloheptan-2-ones.

Depending on dosage form, the pharmaceutical compositions of the present invention may be administered in different ways, i.e. parenterally, topically, or the like. Preferred dosage forms are liquid dosage forms that can be administered parenterally.

The amount of bioactive agent will be dependent upon the particular drug employed and medical condition being treated. Typically, the amount of drug represents about 0.001% to about 70%, more typically about 0.001% to about 50%, most typically about 0.001% to about 20% by weight of the matrix.

The quantity and type of alkyd incorporated into the parenteral will vary depending on the release profile desired and the amount of drug employed. The product may contain blends of polymers to provide the desired release profile or consistency to a given formulation.

The functionalized alkyd polyester, upon contact with body fluids, including blood or the like, undergoes gradual degradation, mainly through hydrolysis, with concomitant release of the dispersed drug for a sustained or extended period, as compared to the release from an isotonic saline solution. This can result in prolonged delivery of effective amounts of drug, e.g. over about 1 to about 2,000 hours, preferably about 2 to about 800 hours, or, e.g. 0.0001 mg/kg/hour to 10 mg/kg/hour. This dosage form can be administered as is necessary, depending on the subject being treated, the severity of the affliction, the judgment of the prescribing physician, and the like.

Individual formulations of drugs and polyether alkyd may be tested in appropriate in vitro and in vivo models to achieve the desired drug release profiles. For example, a drug could be formulated with a functionalized alkyd polyester and orally administered to an animal. The drug release profile could then be monitored by appropriate means, such as by taking blood samples at specific times and assaying the samples for drug concentration. Following this or similar procedures, those skilled in the art will be able to formulate a variety of formulations.

In a further embodiment of the present invention, the polymers and blends thereof can be used in tissue engineering applications, e.g. as supports for cells or delivery vehicle for cells. Appropriate tissue scaffolding structures are known in the art, such as the prosthetic articular cartilage described in U.S. Pat. No. 5,306,311, the porous biodegradable scaffolding described in WO 94/25079, and the prevascularized implants described in WO 93/08850 (all hereby incorporated by reference herein). Methods of seeding and/or culturing cells in tissue scaffoldings are also known in the art such as those methods disclosed in EPO 422 209 B1, WO 88/03785, WO 90/12604 and WO 95/33821, all of which are all hereby incorporated by reference herein as if set forth in their entirety.

In another embodiment, the functionalized alkyd polyester is used to coat a surface of a medical device to enhance the lubricity of the coated surface. The polymer may be applied as a coating using conventional techniques. For example, the polymer may be solubilized in a dilute solution of a volatile organic solvent, such as acetone, methanol, ethyl acetate or toluene, and then the article can be immersed in the solution to coat its surface. Once the surface is coated, the surgical article can be removed from the solution where it can be dried at an elevated temperature until the solvent and any residual reactants are removed.

Although it is contemplated that numerous surgical articles, including but not limited to endoscopic instruments, can be coated with the polymers of this invention to improve the surface properties of the article, the preferred surgical articles are surgical sutures and needles. The most preferred surgical article is a suture, most preferably attached to a needle. Preferably, the suture is a synthetic absorbable suture. These sutures are derived, for example, from homopolymers and copolymers of lactone monomers such as glycolide, lactide, including L-lactide D-lactide, meso-lactide and rac-lactide, $\epsilon$-caprolactone, p-dioxanone, 1,4-dioxanone, 1,4-dioxepan-2-one, 1,5-dioxepan-2-one and trimethylene carbonate. The preferred suture is a braided multifilament suture composed of polyglycolide or poly (glycolide-co-lactide).

The amount of coating polymer to be applied on the surface of a braided suture can be readily determined empirically and will depend on the particular copolymer and suture chosen. Ideally, the amount of coating copolymer applied to the surface of the suture may range from about 0.5 to about 30 percent of the weight of the coated suture, more preferably from about 1.0 to about 20 weight percent, most preferably from 1 to about 5 weight percent. If the amount of coating on the suture were greater than about 30 weight percent, then it may increase the risk that the coating may flake off when the suture is passed through tissue.

Sutures coated with the polymers of this invention are desirable because they have a more slippery feel, thus making it easier for the surgeon to slide a knot down the suture to the site of surgical trauma. In addition, the suture is more pliable and, therefore, is easier for the surgeon to manipulate during use. These advantages are exhibited in comparison to sutures which do not have their surfaces coated with the polymer of this invention.

In another embodiment of the present invention, when the article is a surgical needle, the amount of coating applied to the surface of the article is an amount which creates a layer with a thickness ranging preferably between about 2 to about 20 microns on the needle, more preferably about 4 to about 8 microns. If the amount of coating on the needle were such that the thickness of the coating layer was greater than about 20 microns, or if the thickness was less than about 2 microns, then the desired performance of the needle as it is passed through tissue may not be achieved.

In another embodiment of the present invention, functionalized alkyd polyesters of the present invention can be used to overcoat microparticles encapsulating a bioactive agent(s). This would help provide an additional barrier for sustained release of the drug.

In yet another embodiment, the functionalized alkyd polyesters of the present invention could be used to form a bone replacement material comprising the solid polymer, or the liquid polymer, or a microdispersion of the polymers of the current invention and inorganic filler. The inorganic filler may be selected from alpha-tricalcium phosphate, beta-tricalcium phosphate, calcium carbonate, barium carbonate, calcium sulfate, barium sulfate, hydroxyapatite, and mixtures thereof. In certain embodiments the inorganic filler comprises a polymorph of calcium phosphate. Preferably, the inorganic filler is hydroxyapatite. The bone replacement materials may further comprise a bioactive agent in a therapeutically effective amount, such a growth factor, to facilitate growth of bone tissue. Furthermore, the bone replacement material may comprise a biologically derived substance selected from the group consisting of demineralized bone, platelet rich plasma, bone marrow aspirate and bone fragments. The relative amounts of polymeric wax and inorganic filler may be determined readily by one skilled in the art by routine experimentation after having the benefit of this disclosure.

The injectable microdispersions can be used for a variety of soft tissue repair and augmentation procedures. For example, the microdispersions can be used in facial tissue repair or augmentation, including but not limited to camouflaging scars, filling depressions, smoothing out irregularity, correcting asymmetry in facial hemiatrophy, second branchial arch syndrome, facial lipodystrophy and camouflaging age-related wrinkles as well as augmenting facial eminences, e.g. lips, brow, etc. Additionally, these injectable microdispersions can be used to restore or improve sphincter function, such as for treating stress urinary incontinence. Other uses of these injectable microdispersions may also include the treatment of vesicoureteral reflux (incomplete function of the inlet of the ureter in children) by subureteric injection and the application of these microdispersions as general purpose fillers in the human body.

Surgical applications for an injectable, biodegradable microdispersion include, but are not limited to, facial contouring, e.g. frown or glabellar line, acne scars, cheek depressions, vertical or perioral lip lines, marionette lines or oral commissures, worry or forehead lines, crow's feet or periorbital lines, deep smile lines or nasolabial folds, smile lines, facial scars, lips and the like; periurethral injection, including injection into the submucosa of the urethra along the urethra, at or around the urethral-bladder junction to the external sphincter; urethral injection for the prevention of urinary reflux; injection into the tissues of the gastrointestinal tract for the bulking of tissue to prevent reflux; to aid in sphincter muscle coaptation, internal or external, and for coaptation of an enlarged lumen; intraocular injection for the replacement of vitreous fluid or maintenance of intraocular pressure for retinal detachment; injection into anatomical ducts to temporarily plug the outlet to prevent reflux or infection propagation; larynx rehabilitation after surgery or atrophy; and any other soft tissue which can be augmented for cosmetic or therapeutic effect. Surgical specialists who would use such a product include, but are not limited to, plastic and reconstructive surgeons; dermatologists; facial plastic surgeons, cosmetic surgeons, otolaryngologists; urologists; gynecologists; gastroenterologists; ophthalmologists; and any other physician qualified to utilize such a product.

Additionally, to facilitate the administration and treatment of patients with the inventive microdispersion, pharmaceutically active compounds or adjuvants can be administered therewith. Pharmaceutically active agents that may be co-administered with the inventive microdispersion include, but are not limited to, anesthetics, e.g. lidocaine; and antiinflammatories, e.g. cortisone.

The microdispersion can be administered with a syringe and needle or a variety of devices. It is also envisioned that the microdispersion could be sold in the form of a kit comprising a device containing the microdispersion. The device having an outlet for said microdispersion, an ejector for expelling the microdispersion and a hollow tubular member fitted to the outlet for administering the microdispersion into an animal.

The dosage forms for the microdispersions of the invention are sustained-release parenterals, bioerodible ointments, gels, creams, and similar soft dosage forms.

The examples set forth below are for illustration purposes only and are not intended to limit the scope of the claimed invention in any way. Numerous additional embodiments within the scope and spirit of the invention will become readily apparent to those skilled in the art.

In the examples below, the synthesized polymers were characterized via differential scanning calorimetry (DSC), gel permeation chromatography (GPC), and nuclear magnetic resonance (NMR) spectroscopy. DSC measurements were performed on a 2920 Modulated Differential Scanning Calorimeter from TA Instruments using aluminum sample pans and sample weights of 5–10 milligrams. Samples were heated from room temperature to 100° C. at 10° C./minute; quenched to −40° C. at 30° C./minute followed by heating to 100° C. at 10° C./minute. For GPC, a Waters System with Millennium 32 Software and a 410 Refractive Index Detector were used. Molecular weights were determined relative to polystyrene standards using THF as the solvent. Proton NMR was obtained in deuterated chloroform on a 400 MHz NMR spectrometer using Varian software.

EXAMPLE 1

Synthesis of a Copolymer of Monooleoyl Glyceride and Maleic Anhydride 142.6 grams of monoleoyl glycerol were added to a dry 250 ml, single neck, round bottom flask. A stir bar, was added and a nitrogen inlet adapter was attached. The reaction flask was placed in a room temperature oil bath and a nitrogen gas blanket was started. The flask was heated to 140° C., and 39.2 grams of maleic anhydride were added. The temperature was raised to 190° C. and maintained for 3 hours. After 3 hours the flask was removed from the oil bath to cool to room temperature. The polymer was a pale yellow, viscous liquid. GPC measurement determined a number average molecular weight of 1383, and a weight average molecular weight of 6435.

EXAMPLE 2

Synthesis of Copolymer of Monooleoyl Glyceride and Maleic Anhydride and 5 mol % PEG400

40.1 grams of monooleoyl glycerol and 5.0 grams of PEG400 were added to a dry 100 ml, single neck, round bottom flask. A stir bar was added and a nitrogen inlet adapter was attached. The reaction flask was placed into a room temperature oil bath and a nitrogen blanket was applied. The oil bath temperature was raised to 140° C. Once at 140° C., 12.3 grams of maleic anhydride were added. The temperature was raised to 180° C. and maintained for 7 hours at 180° C. The flask was removed from the oil bath and allowed to cool to room temperature. The polymer was a pale yellow, viscous liquid.

GPC measurement determined a number average molecular weight of 1122, and a weight average molecular weight of 5647.

EXAMPLE 3

Synthesis of Copolymer of Monooleoyl Glyceride and Maleic Anhydride and 25 mol % PEG400

17.8 grams of monooleoyl glycerol and 20.0 grams of PEG400 were added to a dry 100 ml, single neck, round bottom flask. A stir bar was added and a nitrogen inlet adapter was attached. The reaction flask was placed into a room temperature oil bath and a nitrogen blanket was applied. The oil bath temperature was raised to 140° C. Once at 140° C., 9.8 grams of maleic anhydride were added. The temperature was raised to 180° C. and maintained for 7 hours at 180° C. The flask was removed from the oil bath and allowed to cool to room temperature. The polymer was a pale yellow, viscous liquid.

GPC measurement determined a number average molecular weight of 1230, and a weight average molecular weight of 4481.

EXAMPLE 4

Reaction of Mercaptoethanol with Copolymer of Monooleoyl Glyceride and Maleic Anhydride 5.0 grams of a copolymer of monooleoyl glyceride and maleic anhydride made following the procedure of Example 1, 0.77 ml of mercaptoethanol and 11 ml of DMF were added to a dry 50 ml, single neck, round bottom flask along with 52 milligrams of azobis isobutyronitrile (AIBN). A stir bar was added and a nitrogen inlet adapter was attached. The reaction flask was placed in a room temperature oil bath and a nitrogen blanket was started. The temperature was raised to 60° C. and maintained for 24 hours. After 24 hours, the flask was removed from the oil bath to cool to room temperature. The polymer was diluted with 10 mL of ethyl acetate and then washed twice with an aqueous NaCl solution, dried with $MgSO_4$, and filtered through a filter paper. The solvent was removed by rotary evaporation followed by vacuum drying. The polymer was a yellow, transparent viscous liquid.

$^1$H NMR showed that there was no $\alpha,\beta$-unsaturated ester remaining in the polymer (no peak at 6.8 ppm). $^1$H NMR (400 MHz, $CD_3Cl$, ppm): $\delta$ 0.86 triplet (3H), 1.26 multiplet (22H), 1.61 multiplet (2H), 2.00 multiplet (4H), 2.30 multiplet (2H), 2.80 multiplet (3H), 3.00 doublet (2H), 3.80 multiplet (2H), 4.20 multiplet (5H), 5.38 multiplet (2H), 8.00 singlet (1H). IR confirms the presence of hydroxy functional groups. IR (ZnS): 3442, 2920, 2860, 1745, 1456, 1168 cm$^{-1}$.

EXAMPLE 5

Reaction of Mercaptopropionic Acid with Copolymer of Monooleoyl Glyceride and Maleic Anhydride 5.0 grams of copolymer of monooleoyl glyceride and maleic anhydride made following the procedure of Example 1, 0.98 ml of mercaptopropionic acid, and 11 ml of DMF were added to a dry 50 ml, single neck, round bottom flask along with 54 mg (or 3 mole percent) of AIBN. A stir bar was added and a nitrogen inlet adapter was attached. The reaction flask was placed in a room temperature oil bath and a nitrogen blanket was started. The temperature was raised to 60° C. and maintained for 24 hours. After 24 hours, the flask was removed from the oil bath to cool to room temperature. The polymer was diluted with 10 ml of ethyl acetate, washed with 0.01M NaOH, and then washed twice with an aqueous NaCl solution, dried with $MgSO_4$, and filtered through a filter paper. The solvent was removed by rotary evaporation followed by vacuum drying. The polymer was a yellow, transparent viscous liquid.

$^1$H NMR showed that there was no $\alpha,\beta$-unsaturated ester remaining in the polymer (no peak at 6.8 ppm). $^1$H NMR (400 MHz, $CD_3Cl$, ppm): $\delta$ 0.86 triplet (3H), 1.26 multiplet (22H), 1.45 multiplet (3H), 1.61 multiplet (2H), 2.00 multiplet (4H), 2.30 multiplet (2H), 2.90 multiplet (3H), 3.00 doublet (2H), 3.70 multiplet (2H), 4.20 multiplet (5H), 5.38 multiplet (2H), 8.00 singlet (1H). IR confirms the presence of hydroxy functional groups. IR (ZnS): 3437, 3213, 2920, 2860, 1745, 1456, 1168 cm$^{-1}$.

EXAMPLE 6

Reaction of Mercaptoethylamine with Copolymer of Monooleoyl Glyceride and Maleic Anhydride 5.0 grams of copolymer of monooleoyl glyceride and maleic anhydride made following the procedure of Example 1, 0.85 ml of mercaptoethylamine and 11 ml of DMF were added to a dry 50 ml, single neck, round bottom flask along with 54 mg of AIBN. A stir bar was added and a nitrogen inlet adapter was attached. The reaction flask was placed in a room temperature oil bath and a nitrogen blanket was started. The temperature was raised to 60° C. and maintained for 24 hours. After 24 hours, the flask was removed from the oil bath to cool to room temperature. The polymer was diluted with 10 ml of ethyl acetate, washed with 0.01M NaOH, and then washed twice with an aqueous NaCl solution, dried with $MgSO_4$, and filtered through a filter paper. The solvent was removed by rotary evaporation followed by vacuum drying. The polymer was a yellow, transparent viscous liquid.

$^1$H NMR showed that there was no $\alpha,\beta$-unsaturated ester remaining in the polymer (no peak at 6.8 ppm). $^1$H NMR (400 MHz, $CD_3Cl$, ppm): $\delta$ 0.86 triplet (3H), 1.26 multiplet (22H), 1.61 multiplet (2H), 2.00 multiplet (4H), 2.30 multiplet (2H), 2.80 multiplet (2H), 3.60 multiplet (2H), 4.20 multiplet (3H), 5.38 multiplet (2H). IR confirms the presence of amine functional groups. IR (ZnS): 3346, 2920, 2860, 1745, 1660, 1456, 1168 cm$^{-1}$.

EXAMPLE 7

Reaction of O-(2-aminoethyl)-O'-methylpolyethyleneglycol 5000 with Copolymer of Monooleoyl Glycerol and Maleic Anhydride 1.0 gram of poly(glyceryl monooleate-succinate), 11.1 g of O-(2-aminoethyl)-O'-methylpolyethyleneglycol 5000, and 11 ml of DMF were added to a dry 50 ml, single neck, round bottom flask along with 10.8 milligrams of AIBN. A stir bar was added and a nitrogen inlet adapter was attached. The reaction flask was placed in a room temperature oil bath and a nitrogen blanket was started. The temperature was raised to 60° C. and maintained for 24 hours. After 24 hours, the flask was removed from the oil bath to cool to room temperature. The polymer was diluted with 10 ml of ethyl acetate and then washed twice with an aqueous NaCl solution, dried with $MgSO_4$, and filtered through a filter paper. The solvent was removed by rotary evaporation followed by vacuum drying. The polymer was a white solid.

$^1$H NMR showed that there was no $\alpha,\beta$-unsaturated ester remaining in the polymer (no peak at 6.8 ppm). $^1$H NMR (400 MHz, $CD_3Cl$, ppm): $\delta$ 0.86 triplet (3H), 1.26 multiplet (22H), 1.61 multiplet (2H), 2.00 multiplet (4H), 2.20 multiplet (22H), 3.60 multiplet (400H), 5.38 multiplet (2H). IR (ZnS): 3473, 2860, 1745, 1456, 1342, 1282, 1242, 1113, 968, 844 cm$^{-1}$.

I claim:

1. A synthetic polymer comprising the reaction product of an $\alpha$, $\beta$-unsaturated polybasic acid or derivative thereof; and
a monoglyceride;
said polymer comprising an aliphatic polyester backbone with pendant fatty acid ester groups on the monoglyceride unit and further comprising pended thereto a functional agent comprising a first functional nucleophilic moiety and a second functional moiety other than said first functional moiety, said second functional moiety pended to said $\alpha,\beta$-unsaturated polybasic acid or derivative thereof.

2. The polymer of claim 1 wherein said $\alpha,\beta$-unsaturated polybasic acid or derivative thereof is selected from the group consisting of maleic acid, fumaric acic, citraconic acid, itaconic acid, maleic anhydride, mixed anhydrides, esters, activated esters and acid halides.

3. The polymer of claim 1 wherein said monoglyceride is selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol.

4. The polymer of claim 3 wherein said $\alpha,\beta$-unsaturated polybasic acid derivative is maleic anhydride.

5. The polymer of claim 3 wherein said $\alpha,\beta$-unsaturated polybasic acid is maleic acid.

6. The polymer of claim 1 wherein said functional agent is selected from the group consisting of mercaptoethanol, mercaptopropanol, mercaptobutanol, mercaptohexanol, mercaptopropanediol, mercaptoacetic acid, mercaptopropionic acid, mercaptosuccinic acid and mercaptoethylamine.

7. The polymer of claim 1 wherein said polymer is branched.

8. The polymer of claim 1 wherein said polymer comprises the reaction product of said monoglyceride, and at least two of said α,β-unsaturated polybasic acids or derivatives thereof selected from the group consisting of maleic acid, fumaric acic, citraconic acid, itaconic acid, maleic anhydride, mixed anhydrides, esters, activated esters and acid halides.

9. The polymer of claim 1 wherein said polymer comprises the reaction product of said monoglyceride, said α,β-unsaturated polybasic acids or derivatives thereof, and a polybasic acid selected from the group consisting of succinic acid, glutaric acid, adipic acid, pimelic acid, suberic acid and sebacic acid.

10. The polymer of claim 1 wherein said polymer comprises the reaction product of said α,β-unsaturated polybasic acid or derivative thereof, and at least two monoglycerides selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol.

* * * * *